(12) United States Patent
Guggenheim et al.

(10) Patent No.: US 7,772,435 B2
(45) Date of Patent: Aug. 10, 2010

(54) METHOD OF FORMING A DRY QUATERNARY AMMONIUM SALT MIXTURE

(75) Inventors: Thomas Link Guggenheim, Mt. Vernon, IN (US); Paul Edward Howson, Latham, NY (US); Farid Fouad Khouri, Clifton Park, NY (US); Lioba Maria Kloppenburg, Mt. Vernon, IN (US); Matthew Hal Littlejohn, Green Island, NY (US); Jacob Lee Oberholtzer, Evansville, IN (US); Juan Rodriguez Ordonez, Madrid (ES); Suresh R. Sriram, Aurora, IL (US); David Winfield Woodruff, Saratoga Springs, NY (US)

(73) Assignee: Sabic Innovative Plastics IP B.V. (NL)

( * ) Notice: Subject to any disclaimer, the term of this patent is extended or adjusted under 35 U.S.C. 154(b) by 790 days.

(21) Appl. No.: 11/617,416

(22) Filed: Dec. 28, 2006

(65) Prior Publication Data

US 2008/0161576 A1 Jul. 3, 2008

(51) Int. Cl.
*C07C 211/62* (2006.01)
*C07C 251/02* (2006.01)
*C07D 211/00* (2006.01)
*C07D 213/72* (2006.01)

(52) U.S. Cl. .................. 564/248; 564/295; 546/184; 546/304

(58) Field of Classification Search .................. 564/248, 564/295; 546/184, 304
See application file for complete search history.

(56) References Cited

U.S. PATENT DOCUMENTS

| | | | |
|---|---|---|---|
| 4,269,665 A | 5/1981 | Barnes et al. | |
| 4,450,295 A | 5/1984 | van der Mass | |
| 4,460,778 A | 7/1984 | Brunelle | |
| 4,520,204 A | 5/1985 | Evans | |
| 4,554,357 A | 11/1985 | Verbicky, Jr. et al. | |
| 4,577,033 A | 3/1986 | Verbicky, Jr. et al. | |
| 4,595,760 A | 6/1986 | Brunelle | |
| 4,605,745 A | 8/1986 | Brunelle et al. | |
| 5,081,298 A | 1/1992 | Brunelle | |
| 5,116,975 A | 5/1992 | Brunelle | |
| 5,908,915 A | 6/1999 | Brunelle | |
| 7,115,785 B2 | 10/2006 | Guggenheim et al. | |

FOREIGN PATENT DOCUMENTS

EP 0763521 3/1997

OTHER PUBLICATIONS

International Search Report for International Application No. PCT/US2007/074588, mailed Jan. 11, 2008, 6 pages.
Written Opinion for International Application No. PCT/US2007/074588, mailed Jan. 11, 2008, 7 pages.
Fu, Jiquan. Salt Efect on Vapor-Liquid Equilibria for Binary Systems of Propanol/CaCl2 and Butanol/CaCl2. Fluid Phase Equilibria, vol. 237. pp. 219-2233, 2005 .
Armarego, W.L.F. and Dr. Christina Chai. Common Physical Techniques Used in Purification. "Purification of Laboratory Chemicals", 2003. pp. 1-14.

*Primary Examiner*—Shailendra Kumar
(74) *Attorney, Agent, or Firm*—Cantor Colburn LLP

(57) ABSTRACT

Disclosed herein is a method comprising:
(a) adding an aqueous solution comprising a quaternary ammonium salt to an organic solvent in a vessel under an inert atmosphere, thereby forming a first mixture comprising the quaternary ammonium salt and the solvent; and
(b) mixing the first mixture at a temperature and for a time sufficient to remove water and a portion of the solvent from the first mixture,
wherein the mixing is performed in an inert atmosphere and the temperature is less than the decomposition temperature of the quaternary ammonium salt.

32 Claims, No Drawings

METHOD OF FORMING A DRY QUATERNARY AMMONIUM SALT MIXTURE

BACKGROUND OF INVENTION

This disclosure is related to removing water from quaternary ammonium salts.

Quaternary ammonium salts are used in a wide variety of reactions. Frequently quaternary ammonium salts are used as phase transfer catalysts. In some reactions the presence of water in the phase transfer catalyst decreases the amount of product produced by the reaction or, in some cases, prevents the reaction from occurring. While quaternary ammonium salts can be used in solid form, the solid form can contain water as many quaternary ammonium salts absorb water from the atmosphere. Straightforward methods of drying the quaternary ammonium salt solid such as heating in an oven can result in the formation of significant amounts of degradation products, which can then interfere with or negatively influence subsequent reactions. Additionally when the quaternary ammonium salt is used as a catalyst for commercial scale reactions it can be difficult to accurately add the solid material to the reaction vessel.

There remains a need in the art for drying quaternary ammonium salts, particularly dry quaternary ammonium salts that are substantially free of degradation products and are in a form suitable for use with commercial scale reactions.

BRIEF DESCRIPTION OF THE INVENTION

The aforementioned needs are met by a method comprising:
(a) adding an aqueous solution comprising a quaternary ammonium salt to an organic solvent in a vessel under an inert atmosphere, thereby forming a first mixture comprising the quaternary ammonium salt and the solvent; and
(b) mixing the first mixture at a temperature and for a time sufficient to remove water and a portion of the solvent from the first mixture,
wherein the mixing is performed in an inert atmosphere and the temperature is less than the decomposition temperature of the quaternary ammonium salt.

In another embodiment, a method comprises:
(a) combining an aqueous solution comprising a quaternary ammonium salt and an inorganic salt with an aliphatic chlorinated solvent, thereby forming a first phase comprising water and inorganic salt and a second phase comprising chlorinated aliphatic solvent and the quaternary ammonium salt;
(b) separating the first phase from the second phase;
(c) adding the second phase to an organic solvent in a vessel under an inert atmosphere, thereby forming a first mixture comprising the quaternary ammonium salt, trace water, and the solvent; and
(d) mixing the first mixture at a temperature and for a time sufficient to remove trace water, chlorinated aliphatic solvent and a portion of the organic solvent from the first mixture,
wherein the mixing is performed in an inert atmosphere and the temperature is less than the decomposition temperature of the quaternary ammonium salt.

DETAILED DESCRIPTION OF THE INVENTION

Obtaining quaternary ammonium salts that are sufficiently dry and contain little or no degradations products, particularly in a form suitable for use in commercial scale reactions has been challenging. Described herein is a method of drying the quaternary ammonium salts without substantial degradation and which has the added benefit of resulting in a form suitable for use in commercial scale reactions.

Quaternary ammonium salts include bis-guanidinium alkane salts, dialkylaminopyridinium salts, bis-dialkylaminopyridinium salts, dialkyl heterocycloaliphatic salts, bis-alkyl quaternary ammonium salts, guanidinium alkane salts (mono guanidinium salts), e.g., hexaethylguanidinium chloride (HEGCl), and combinations of two or more of the foregoing. Salts are frequently referred to by the identity of the counter ion and as such the quaternary ammonium salt may be a halide salt, nitrate salt, nitrite salt, boron-containing salt, antimony-containing salt, phosphate salt, a carbonate salt, a carboxylate salt or a combination of two or more of the foregoing.

Bis-guanidinium alkane salts have the formula (I):

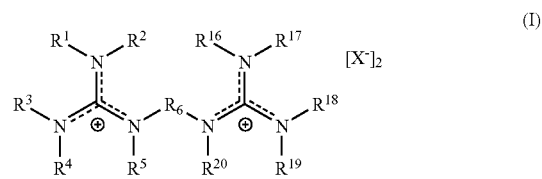

wherein $R^{1-5}$ and $R^{16-20}$ are each independently selected from the group comprising alkyl, cyclo alkyl, aryl, and aryl alkyl and have 1 to 20 carbons. $R^6$ is an alkyl group having 2 to 12 carbons, or, more specifically, 4 to 8 carbons. In some embodiments $R^{1-5}$ and $R^{16-20}$ are each independently alkyl groups having 1 to 12, or, more specifically, 2 to 6 carbons. In some embodiments $R^6$ is non-branched. $X^-$ can be any suitable anion referred to in the preceding paragraph and in some embodiments is the anion of a strong acid such as chloride or bromide.

Dialkylaminopyridinium salts have the formula (II):

wherein $R^7$ and $R^8$ are hydrocarbyl groups having 1 to 13 carbons. The hydrocarbyl groups may be substituted or unsubstituted and branched or not branched. $R^7$ and $R^8$ together can form a cyclic hydrocarbyl group. $R^9$ is a linear or branched alkyl group having 4 to 12 carbons. $X^-$ is as defined above.

Dialkylaminopyridinium salts have the formula (III):

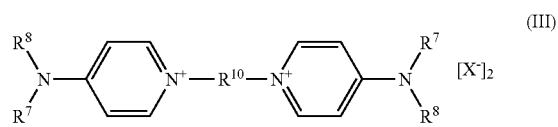

wherein $R^7$, $R^8$, and $X^-$ are defined as above. $R^{10}$ is a linear hydrocarbyl having 4 to 25 carbon atoms.

Dialkyl heterocycloaliphatic salts have the formula (IV):

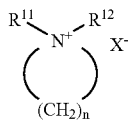

(IV)

wherein $R^{11}$ and $R^{12}$ are each independently an alkyl groups having 1 to 4 carbons and n equals 4 to 6. $X^-$ is defined as above.

Bis-alkyl quaternary ammonium salts have the formula (V):

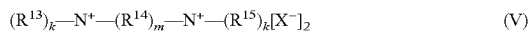

(V)

wherein $R^{13}$ and $R^{15}$ are each independently an alkyl having 1 to 12 carbons, each $R^{14}$ is a hydrocarbyl group having 1 to 12 carbons with the proviso that all $R^{14}$ groups, taken together, have 4 to 12 carbons, k equals 1 to 3, and m equals 4-k with the proviso that at least three of the $R^{13}$, $R^{14}$ and $R^{15}$ are aliphatic or alicyclic.

Guanidinium alkane salts have the formula (VI):

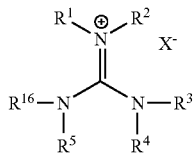

(VI)

wherein $R^{1-5}$, $R^{16}$, and X are defined as above. In some embodiments the guanidinium alkane salt is hexaethylguanidinium chloride.

The aqueous solution comprises the quaternary ammonium salt in amounts of 1 to 90 weight percent, or, more specifically, 10 to 80 weight percent, or, even more specifically, 20 to 50 weight percent, based on the total weight of the solution. The aqueous solution may additionally comprise an inorganic salt, such as sodium chloride, potassium chloride and the like. The inorganic salt may be present in an amount of 0.1 to 20 weight percent, or, more specifically, 3 to 15 weight percent, based on the total weight of the aqueous solution.

The aqueous solution is added to an organic solvent in a vessel under an inert atmosphere to form a mixture. Exemplary vessels include those described in U.S. Pat. No. 7,115,785. Exemplary organic solvents include halogenated aromatics, alkylated aromatics, ether aromatics, and combinations of two or more of the foregoing. In some embodiments the organic solvent comprises orthodichlorobenzene, veratroles, anisoles, toluenes, xylenes, chlorobenzenes, benzenes, or a combination of two or more of the foregoing. When more than one organic solvent is used at least one of the organic solvents is capable of forming an azeotrope with water.

The volume to volume ratio of organic solvent to aqueous solution can be greater than or equal to 5 to 1, or, more specifically, greater than or equal to 8 to 1, or, even more specifically greater than or equal to 10 to 1. The maximum volume to volume ratio can be 1000 to 1.

The inert atmosphere can be a gas such as nitrogen or combination of gasses (including nitrogen) that are inert to the reactants. The gas or combination of gasses can be introduced to the vessel either above or below the level of the mixture inside the vessel. In some embodiments the flow rate of the gas or combination of gasses into the vessel is sufficient to facilitate water removal from the mixture in the vessel.

The mixture is mixed at a temperature and for a time sufficient to remove water and a portion of the organic solvent from the mixture. The removed solvent may be condensed, separated from bulk water, and recycled to the mixture. In some embodiments the removed solvent is condensed in a first condenser, distilled to remove water and the removed water is condensed in a second condenser. Additional solvent may also be added. The temperature is less than the decomposition temperature of the quaternary ammonium salt. Exemplary temperatures are 70° C. to 230° C. In some embodiments the organic solvent is heated, for example to a temperature of 70° C. to 230° C., prior to the addition of the aqueous solution. Mixing may be performed for 1 minute to 24 hours. The length of time is chosen, along with other parameters, to reduce the amount of water in the mixture to the desired levels. A drying agent can be added to the mixture during or after mixing, and before or after separation of the precipitated inorganic salt. Exemplary drying agents include activated molecular sieves, anhydrous $MgSO_4$, anhydrous $NaSO_4$ and anhydrous CaSO4.

The aqueous solution may be added to the solvent under pressures of 10 millimeters of mercury (mm of Hg) to 1520 mm of Hg, or, more specifically, 50 to 300 mm of Hg, or, even more specifically, 75 to 150 mm of Hg. Additionally mixing can occur at pressures of 10 millimeters of mercury (mm of Hg) to 1520 mm of Hg, or, more specifically, 50 to 300 mm of Hg, or, even more specifically, 75 to 150 mm of Hg. Additionally the aqueous solution may be added to the organic solvent in a single addition, incrementally (in multiple additions), or continuously. When added continuously the rate of addition can be, for example, 0.015 to 0.035 weight percent per minute based on the total volume of organic solvent. For example, 3 to 7 kilograms per minute of aqueous solution can be added to a vessel containing 2000 kilograms of organic solvent to eventually get a mixture that is 20 wt % catalyst (e.g., HEGCl) in the organic solvent, based on the combined weight of catalyst and organic solvent. The mixture can be heated during the addition resulting in the simultaneous removal of water and solvent. Additional organic solvent can be added to maintain the amount of organic solvent at a constant level during the addition of the aqueous solution.

When the aqueous solution comprises an inorganic salt the inorganic salt can be removed in various ways. In some embodiments the inorganic salt can be precipitated upon removal of water and then removed by filtration or other solid/liquid separation technique. In some embodiments the inorganic salt can be agglomerated, for example by removing a sufficient amount of water for the inorganic salt to agglomerate to form large, easily filtered particles. In some embodiments the bulk water is removed and a small amount of water is added back to the solution to obtain the desired large, easily filtered particles. Without being bound by theory it is believed that the rate of water removal, the amount of water removed, and the mixing speed can influence the size of the inorganic salt particles. Once the inorganic salt has been agglomerated it can be removed by a suitable solid/liquid separation technique. In some embodiments decomposition products are associated with the inorganic salt and can be removed or reduced during removal of the inorganic salt.

In some embodiments the aqueous solution of catalyst which may also comprise an inorganic salt is combined with an aliphatic chlorinated solvent thereby forming two phases. The bulk water and inorganic salt are in one phase and the chlorinated aliphatic solvent and quaternary ammonium salt are in the other phase. The phases can then be separated and the phase containing the quaternary ammonium salt is added to the organic solvent as described above. Exemplary chlorinated aliphatic solvents include methylene chloride, chloroethane derivatives (mono chloroethane and polychloroethanes such as dichloroethane, trichloroethane and tetrachloroethane), tetrachloro methylene, chloroform and combinations of two or more of the foregoing.

The methods described herein are capable of reducing the amount of water in a quaternary ammonium salt with less than a 10 weight percent loss, or, more specifically, less than a 5 weight percent loss, of quaternary ammonium salt to decomposition. Additionally the resulting mixture of organic solvent and quaternary ammonium salt can comprise less than or equal to 200 part by weight of water per million parts by weight of solution (ppm), or, more specifically, less than or equal to 100 ppm of water, or, more specifically, less than or equal to 50 ppm of water, or, even more specifically, less than or equal to 25 ppm of water. In some embodiments the mixture of organic solvent and quaternary ammonium salt can have a solids content of 1 to 50 weight percent, or, more specifically 10 to 30 weight percent, based on the total weight of the mixture.

Additionally, an additional compound, such as a monomer for use in a polymerization reaction or a reactant used in reaction requiring a phase transfer catalyst can be added to the mixture comprising the quaternary ammonium salt and organic solvent and further mixed for a time and at a temperature to remove sufficient trace water to result in a mixture which has less than or equal to 50 part by weight of water per million parts by weight of solution (ppm), or, more specifically, less than or equal to 25 ppm of water.

The method is further demonstrated by the following non-limiting examples.

EXAMPLES

In the following examples the following terms may be used:

ODCB stands for orthodichlorobenzene, water or DI water, as used herein, unless specified otherwise, is deionized water, and hexaethylguanidinium chloride (HEGCl) brine solution was a solution of a hexaethylguanidinium chloride comprising approximately 35 weight percent HEGCl, and approximately 10 weight percent sodium chloride, and the remainder comprising water (weight percents based on the total weight of the solution).

Example 1

A 1000 milliliter (mL), 3-necked, round-bottomed flask, was equipped with a magnetic stir bar, a reflux condenser, an external temperature controlled oil bath, a receiver topped with a reflux condenser, and a nitrogen gas sweep. The receiver was configured such that the bottom layer of ODCB that collected in the receiver was diverted back into the vessel with a three-way valve. The receiver was also modified to include an additional cooler.

The bulk water was removed as follows: The vessel was charged with 200 grams of aqueous HEGCl brine solution. The flask was then charged with 400 grams of ODCB. The solution was stirred magnetically. The temperature of the oil bath was slowly raised to 120° C. to 140° C. at which point the water/ODCB azeotrope began to distill overhead. The vapor condensed and formed two layers in the receiver. The ODCB phase that collected in the receiver was allowed to return to the vessel, and the water was drawn off to an external flask. Then the oil bath was slowly heated to 170° C. and the bulk of the water was collected overhead and removed from the system. At this time, sodium chloride precipitated from solution.

Additional ODCB (300 grams) was added to the flask and the temperature of the oil bath was taken to 200° C., where upon the ODCB began to distill overhead. The condensed ODCB overheads were drawn off the system and not allowed to return to the vessel. A slight nitrogen sweep was applied to assist the removal of the ODCB and water. Distillation continued until a total of 300 grams of ODCB was distilled off the vessel. The pot was then sampled for moisture determination by Karl Fischer titration.

The resulting slurry was then vacuum filtered under nitrogen through a 1 micron filter at 25 to 150° C. to remove the precipitated sodium chloride, and afforded a clear ODCB solution of HEGCl at a concentration of 15 weight % with respect to total solution weight. The material thus obtained was found to further contain other components in the amounts shown in Table 1.

TABLE 1

| Component | Amount in Solution, ppm |
|---|---|
| Water | Less than 200 |
| sodium chloride | Less than 100 |
| Diethylamine | Less than 200 |
| Tetraethylurea | Less than 200 |
| Pentaethylguanidine | Less than 300 |

The amount of the components set forth in Table 1 was determined by inductively coupled plasma (ICP) for sodium, ion chromatography (IC) for chloride and, gas chromatography analysis for the diethylamine, tetraethylurea and pentaethylquanidine. As can be seen from Table 1 the method described herein yielded dry HEGCl with little or no decomposition product.

Example 2

The procedure in Example 1 was followed, using the same proportions specified in Example 1, except that the aqueous HEGCl brine solution was slowly added to ODCB that was already maintained at 120° C. to 180° C. The water/ODCB was taken overhead and the condensed ODCB phase returned to the vessel to maintain an optimal operating level and concentration of HEGCl in ODCB. Once the bulk water was removed, dry ODCB was added to the vessel and ODCB distilled overhead until the water in the pot was less than about 30 ppm. The sodium chloride was removed by the method described in example 1.

Example 3

The procedure in Example 1 for removal of bulk water was followed. After the removal of the bulk water the sodium chloride (which had agglomerated) was filtered off to afford a wet ODCB/HEGCl solution that contained about 10,000 ppm to 1000 ppm water. The wet filtered ODCB/HEGCl solution was further dried by distillation of ODCB, while maintaining the concentration of the HEGCl solution at 15 weight % by the addition of dry ODCB while ODCB is being distilled off, to afford an ODCB/HEGCl solution containing less than about 30 ppm water.

Example 4

In this example, a wet catalyst isolated after filtration in Example 3 was dried with 4,4'-dichlorobisimide (ClPAMI shown below). A 1000 mL round-bottomed flask, equipped with a mechanical stirrer, means for a nitrogen atmosphere, a side addition funnel, and a distillation head, was charged with 500 grams of dry ClPAMI slurry (85 grams [194.4 mmol] of ClPAMI and 415 grams of ODCB). An additional 200 grams of ODCB was added to the vessel. At this point 2.56 grams of ODCB HEGCl solution (20% solids, 0.51 grams of HEGCl, 1.94 mmol) from which the bulk water had already been removed was added to the vessel. The contents were heated and 200 grams of ODCB was removed to afford a dry ODCB solution of ClPAMI containing HEGCl and less than 100 ppm of water. This material was then ready for polymerization by the addition of a comonomer.

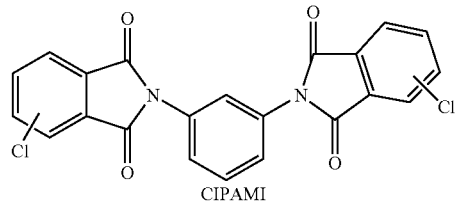

ClPAMI

Example 5

The bulk water was removed from a HEGCL brine solution as described in example 1. Trace water was then removed at a pressure of 90 millimeters (mm) of mercury (Hg) at a temperature of 140-150° C. The sodium chloride precipitated from solution and was then filtered as described in Example 1. The water content was less than 100 ppm.

Example 6

A 37.8 liter (10 gallon) stainless steel reactor was charged with approximately 22 kilograms (kg) of an aqueous brine solution of HEGCl (35% in HEGCl and 6%-14% in NaCl) and 25 kg of dichloromethane. The mixture was stirred for about 30-35 minutes at a temperature of 20-28° C. range. Stirring was stopped and the mixture was allowed to settle for 2 hours to afford two clean phases with a sharp interface. The lower organic layer was removed and the aqueous layer was extracted with 12 liters of dichloromethane. The first organic layer was then charged to a clean 10 gallon stainless steel reactor and was gently heated to distill 17.3 kg of solvent at about 42° C. at atmospheric pressure. Subsequently, 25 kg of ODCB was added to the vessel and the mixture was sparged with nitrogen at 40° C. for 20 minutes. Heating was resumed while keeping the solution under a nitrogen atmosphere to remove 12.6 kg of additional distillate. Karl Fisher titration showed 12 ppm water in distillate coming off at the end of distillation. Temperature gradually reached 180° C. as dichloromethane content was reduced.

The solution was cooled to room temperature and drained into containers while still maintaining nitrogen sparging and stored over 4 Å Molecular Sieves. The water content of the HEGCl solution, measured by direct injection of a HEGCl/ODCB into a Karl Fischer titrator, was in the range of about 190 ppm to about less than 40 ppm within a few days. The ODCB solution contained 27.7 weight % HEGCl and the recovered yield of HEGCl was 98%.

Example 7

A 1000-mL, 3-necked, round-bottomed flask, was equipped with a magnetic stir bar, a reflux condenser, an external temperature controlled oil bath, a receiver topped with a reflux condenser, and a nitrogen gas sweep. The receiver was configured such that the bottom layer of ODCB that collected in the receiver was diverted back into the vessel with a three-way valve. The receiver also was modified to include an additional cooler.

The bulk water was removed as follows: The vessel was charged with 200 grams of aqueous HEGCl brine solution (70 grams dry weight of HEGCl). The flask was then charged with 400 grams of ODCB. The solution was stirred magnetically. The temperature of the oil bath was slowly raised to 120° C. to 140° C. at which point the water/ODCB azeotrope began to distill overhead. The vapor condensed and formed two layers in the receiver. The ODCB phase that collected in the receiver was allowed to return to the vessel and the water was drawn off to an external flask. Then the oil bath was slowly heated to 140° C. and the bulk of the water was collected overhead and removed from the system. At this time, sodium chloride precipitated from solution.

The trace water was removed as follows: 300 grams of toluene was carefully added to the flask and the temperature of the oil bath was taken to 140° C., where upon the toluene distilled off overhead. The toluene condensed overhead was drawn off the system and not allowed to return to the vessel. A slight nitrogen sweep was applied to assist the removal of the toluene. Distillation was continued until a total of 300 grams of toluene is distilled off the vessel. The pot was then sampled for moisture determination by Karl Fischer titration. Water content was less than 100 ppm.

Example 8

This example was performed exactly as example 7 with the exception that benzene was used in the place of toluene. Water content was less than 100 ppm.

Example 9

This example was performed exactly as example 7 with the exception that xylene was used in the place of toluene. Water content was less than 100 ppm.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

All cited patents, patent applications, and other references are incorporated herein by reference in their entirety.

What is claimed is:

1. A method of forming quaternary ammonium salt mixture, comprising:
   (a) adding an aqueous solution comprising a quaternary ammonium salt to an organic solvent in a vessel under an inert atmosphere, thereby forming a first mixture comprising the quaternary ammonium salt and the solvent; and
   (b) mixing the first mixture at a temperature and for a time sufficient to remove water and a portion of the solvent from the first mixture,
   wherein the mixing is performed in an inert atmosphere and the temperature is less than the decomposition temperature of the quaternary ammonium salt, and
   wherein the quaternary ammonium salt is selected from the group consisting of guanidinium salts, bis-guanidinium alkane salts, dialkylaminopyridinium salts, bis-dialkylaminopyridinium salts, dialkylpiperidinium salts, bis-alkyl quaternary ammonium salts, and combinations of two or more of the foregoing.

2. The method of claim 1, wherein the aqueous solution further comprises an inorganic salt and the method further comprises precipitating the inorganic salt from the first mixture and removing the precipitated inorganic salt from the first mixture, thereby forming a second mixture.

3. The method of claim 2, wherein removing the precipitated inorganic salt comprises filtering.

4. The method of claim 2, wherein the second mixture contains less than 50 parts per million of water.

5. The method of claim 2, wherein the second mixture contains less than 25 parts per million of water.

6. The method of claim 2, wherein the method further comprises adding a drying agent to the second mixture.

7. The method of claim 2, wherein the method further comprises combining the second mixture with an additional compound, thereby forming a third mixture, and drying the third mixture to remove trace water.

8. The method of claim 1, wherein the aqueous solution further comprises an inorganic salt and the method further comprises agglomerating the inorganic salt.

9. The method of claim 1, wherein the quaternary ammonium salt has formula (II):

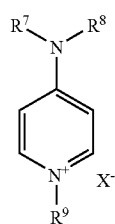

(II)

wherein $R^7$ and $R^8$ are hydrocarbyl groups having 1 to 13 carbons, $R^9$ is a linear or branched alkyl group having 4 to 12 carbons, and $X^-$ is the anion of a strong acid.

10. The method of claim 1, wherein the quaternary ammonium salt is hexaethylguanidinium chloride.

11. The method of claim 1, wherein the temperature is 70° C. to 230° C.

12. The method of claim 1, wherein adding is performed at a pressure of 50 millimeters of mercury to 300 millimeters of mercury.

13. The method of claim 1, wherein the mixing is performed at a pressure of 50 millimeters of mercury to 300 millimeters of mercury.

14. The method of claim 1, wherein the time is 1 minute to 24 hours.

15. The method of claim 1, wherein the solvent is selected from the group consisting of halogenated aromatics, alkylated aromatics, ether aromatics, and combinations thereof.

16. The method of claim 15, wherein the solvent is an aromatic organic solvent selected from the group consisting of orthodichlorobenzene, veratroles, anisoles, toluenes, xylenes, chlorobenzenes, benzenes, and combinations of two or more of the foregoing.

17. The method of claim 1, wherein the quaternary ammonium salt is selected from the group consisting of halide salts, nitrate salts, nitrite salts, boron-containing salts, antimony-containing salts, phosphate salts, carbonate salt, carboxylate salt, and combinations of two or more of the foregoing.

18. The method of claim 1, wherein the aqueous solution is added to the solvent incrementally.

19. The method of claim 1, wherein the aqueous solution is added to the solvent continuously.

20. The method of claim 1, wherein the solvent is heated prior to adding the aqueous solution.

21. The method of claim 1, wherein the solvent is heated to a temperature of 70° C. to 230° C. prior to adding the aqueous solution.

22. The method of claim 1, wherein less than 10 weight percent of the quaternary ammonium salt, based on the total initial weight of the quaternary ammonium salt is decomposed during the method.

23. The method of claim 1, wherein the inert atmosphere is nitrogen and the nitrogen flows into the vessel at a rate sufficient to facilitate removal of the water.

24. The method of claim 1, wherein the method further comprises condensing the removed solvent, removing water from the condensed solvent and recycling the dried condensed solvent.

25. The method of claim 24, wherein the method further comprises condensing organic solvent with a first condenser and condensing water in a gaseous phase in a second condenser.

26. The method of claim 1, wherein the quaternary ammonium salt has formula (VI):

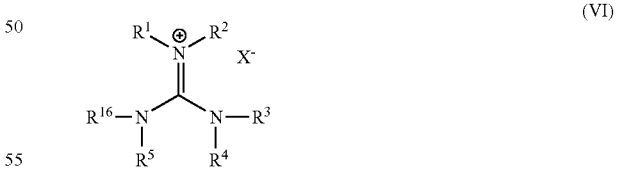

(VI)

wherein and $R^{1-5}$ and $R^{16}$ are each independently selected from the group comprising alkyl, cyclo alkyl, aryl, and aryl alkyl and have 1 to 20 carbons and $X^-$ is an anion of a strong acid.

27. A method of forming quaternary ammonium salt mixture, comprising:
   (a) combining an aqueous solution comprising a quaternary ammonium salt and an inorganic salt with an aliphatic chlorinated solvent, thereby forming a first phase comprising water and inorganic salt and a second phase comprising chlorinated aliphatic solvent, trace water and the quaternary ammonium salt;

(b) separating the first phase from the second phase;

(c) adding the second phase to an organic solvent in a vessel under an inert atmosphere, thereby forming a first mixture comprising the quaternary ammonium salt, trace water, and the solvent; and (d) mixing the first mixture at a temperature and for a time sufficient to remove water, chlorinated aliphatic solvent and a portion of the solvent from the first mixture, wherein the mixing is performed in an inert atmosphere and the temperature is less than the decomposition temperature of the quaternary ammonium salt.

28. The method of claim 27, wherein the chlorinated aliphatic solvent is selected from the group consisting of methylene chloride, chloroethane derivatives, tetrachloro methylene, chloroform, and combinations of two or more of the foregoing.

29. The method of claim 1, wherein the first mixture comprises an inorganic salt in an amount of 0.1 to 20 weight percent.

30. The method of claim 29, wherein the mixture is further mixed for a time and at a temperature sufficient to remove trace water to result in a mixture having less than or equal to 50 ppm water.

31. The method of claim 30, wherein the mixture is further mixed for a time and at a temperature sufficient to remove trace water to result in a mixture having less than or equal to 25 ppm water.

32. The method of claim 1, wherein the method further comprises combining the second mixture with an additional compound, thereby forming a third mixture, and drying the third mixture to remove trace water.

* * * * *